(12) United States Patent
Nakanishi et al.

(10) Patent No.: US 7,044,379 B2
(45) Date of Patent: May 16, 2006

(54) INFORMATION MANAGEMENT SYSTEM, INFORMATION PROCESSING APPARATUS AND METHOD, RECORDING MEDIUM, AND PROGRAM

(75) Inventors: Toshiaki Nakanishi, Chiba (JP); Hiroaki Takano, Kanagawa (JP); Mitsuhiro Isogai, Tokyo (JP); Hiroshi Takeuchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 10/217,983

(22) Filed: Aug. 13, 2002

(65) Prior Publication Data

US 2003/0047600 A1   Mar. 13, 2003

(30) Foreign Application Priority Data

Aug. 14, 2001 (JP) ............................. 2001-245995

(51) Int. Cl.
*G06K 7/10* (2006.01)
(52) U.S. Cl. ............................ 235/462.01; 235/462.09; 235/380
(58) Field of Classification Search ................ 235/375, 235/380, 382, 383, 486, 462.01, 462.09; 283/61; 705/1
See application file for complete search history.

(56) References Cited

U.S. PATENT DOCUMENTS

| | | | | |
|---|---|---|---|---|
| 4,632,428 A * | 12/1986 | Brown | ........................ | 283/76 |
| 4,730,849 A * | 3/1988 | Siegel | ........................ | 283/70 |
| 5,071,168 A * | 12/1991 | Shamos | ........................ | 283/117 |
| 5,193,855 A * | 3/1993 | Shamos | ........................ | 283/117 |
| 5,381,487 A * | 1/1995 | Shamos | ........................ | 382/115 |
| 5,528,021 A * | 6/1996 | Lassus et al. | ................ | 235/380 |
| 5,848,426 A * | 12/1998 | Wang et al. | ................ | 715/505 |
| 5,879,453 A * | 3/1999 | Streeter et al. | ............ | 118/31.5 |
| 5,913,542 A * | 6/1999 | Belucci et al. | ................ | 283/75 |
| 5,973,799 A * | 10/1999 | Gatto et al. | ................. | 358/498 |
| 5,988,898 A * | 11/1999 | Ackley | ........................ | 400/61 |
| 6,112,986 A * | 9/2000 | Berger et al. | ................ | 235/380 |
| 6,286,761 B1 * | 9/2001 | Wen | ........................... | 235/468 |
| 6,379,059 B1 * | 4/2002 | Kaplan | ........................ | 400/76 |
| 6,497,358 B1 * | 12/2002 | Walsh | ........................ | 235/380 |
| 6,513,710 B1 * | 2/2003 | Haas | ........................... | 235/380 |
| 6,775,774 B1 * | 8/2004 | Harper | ........................ | 713/186 |

\* cited by examiner

*Primary Examiner*—Ahshik Kim
(74) *Attorney, Agent, or Firm*—Robert J. Depke; Trexler, Bushnell, Giangiorgi, Blackstone & Marr, Ltd.

(57) ABSTRACT

In an information management system, a patient operates a button of an identification number issuing apparatus installed in the reception area in a hospital and receives a ticket from a ticket slot. The ticket has the patient's identification number printed thereon. Having received the ticket, the patient moves to a photograph booth, operates an identification number input panel to input the identification number printed on the ticket, and takes a photograph of the patient's upper body. The patient receives a photograph/bar code sheet ejected from the photograph booth. Four pairs including photographs and bar codes, which are vertically arranged so as to be associated with each other, are printed on the photograph/bar code sheet. Having received the photograph/bar code sheet, the patient moves to the reception and submits the photograph/bar code sheet and a health insurance card to an attendant at the reception.

22 Claims, 15 Drawing Sheets

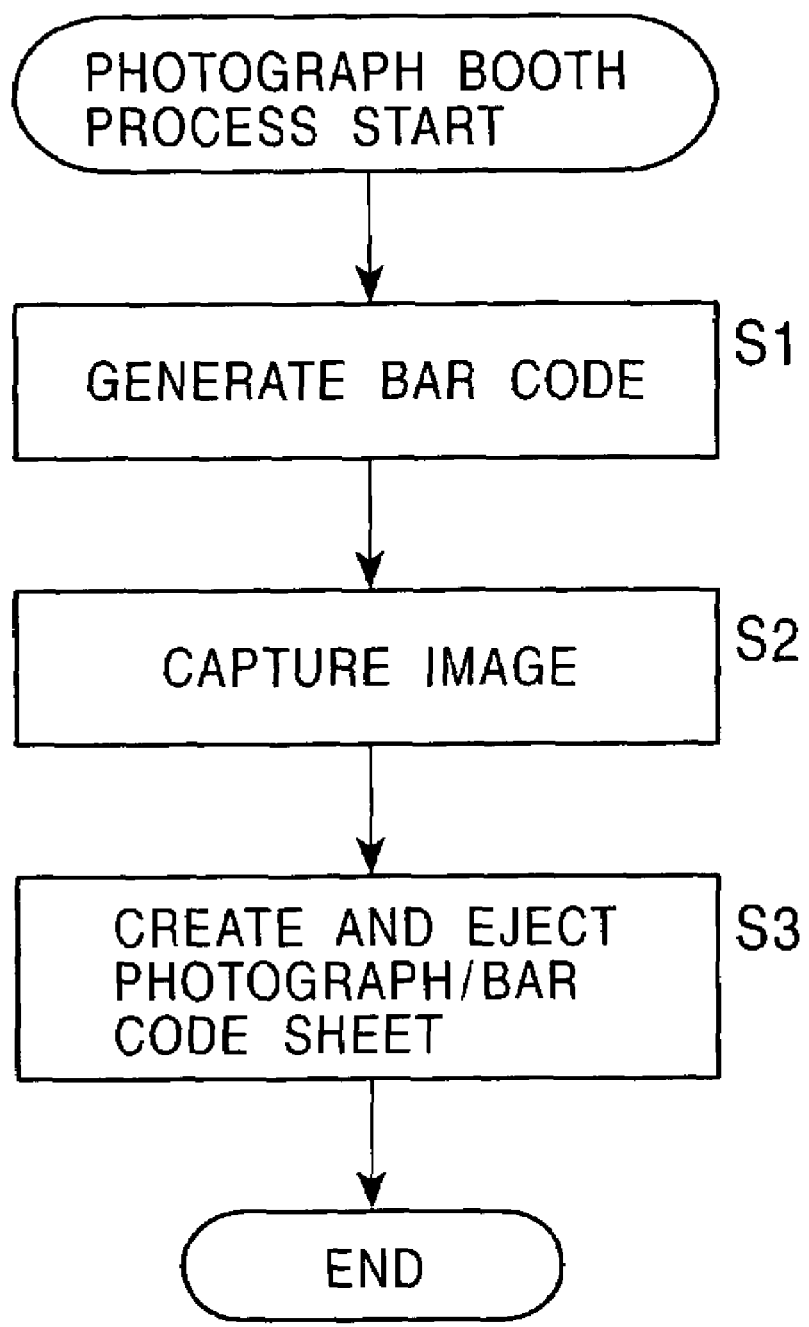

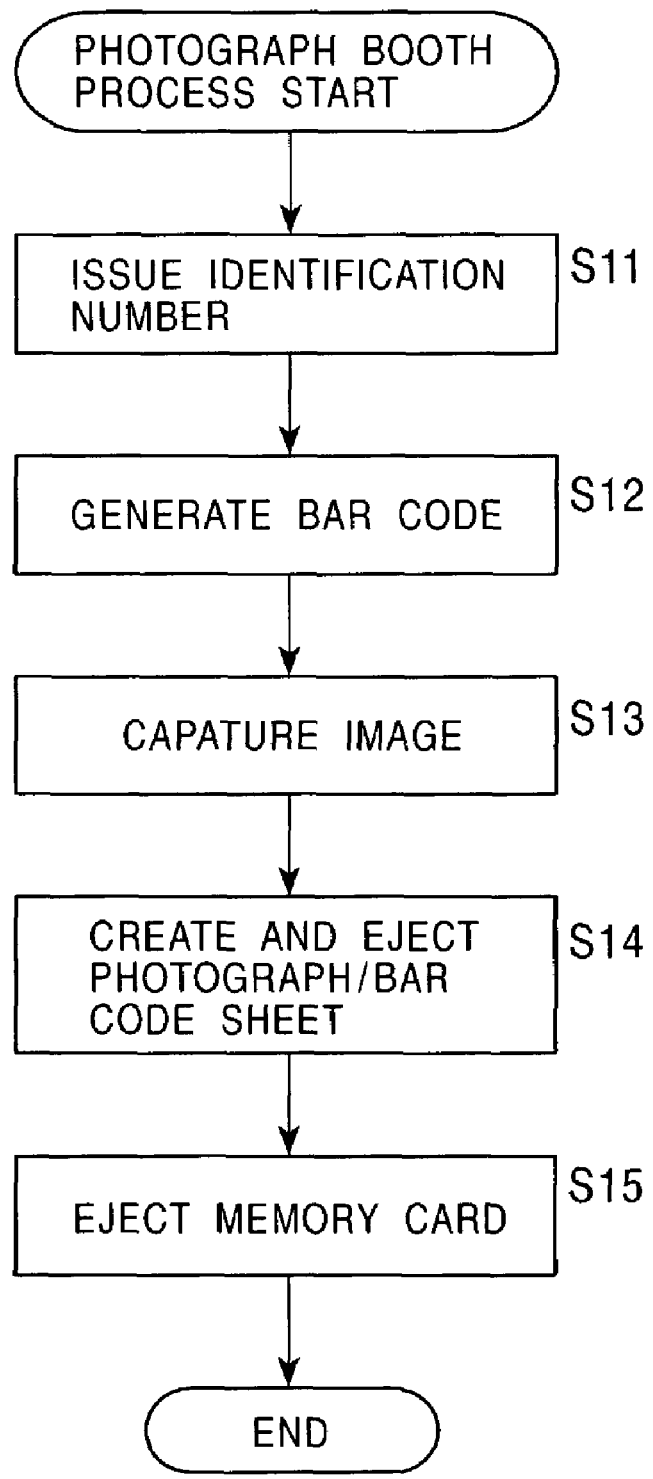

INFORMATION MANAGEMENT SYSTEM, INFORMATION PROCESSING APPARATUS AND METHOD, RECORDING MEDIUM, AND PROGRAM

This application claims priority to Japanese Patent Application Number JP2001-245995 filed Aug. 14, 2001 which is incorporated herein by reference.

BACKGROUND OF THE INVENTION

1. Field of the Invention

The present invention relates to information management systems, information processing apparatuses and methods, recording media, and programs, and particularly relates to, for example, an information management system for preventing the creation of management information for one person under management indicating identification information and a photograph of another, different person under management, to an information processing apparatus and method, a recording medium, and a program.

2. Description of the Related Art

Currently, as methods for preventing patients from getting mixed up with other patients in hospitals, for example, the following methods have been developed. For example, patients are instructed to wear bar-coded wristbands, which indicate patient identification information. Also, documents describing medical treatment (e.g., patients' charts) have bar codes printed thereon, and the bar codes are referenced. Accordingly, patient mix-up is prevented.

However, in the known methods, for example, wristbands and patients' charts only have bar codes and text information such as names recorded thereon. If a wrong bar code is issued to a patient, that patient may be mixed up with other patients unless a nurse or a doctor asks the patient to confirm the patient's name.

In order to solve the problem, a method for visually confirming the identity of a patient by using a patient's photograph has been considered. For example, a patient's identification information is written by hand at the chart, and that patient's photograph is separately pasted by hand onto the same chart (the patient's identification information is written on the chart with a pen, and the patient's photograph is glued onto the chart). A wrong chart having identification information and a photograph of a different patient may be created. As a result, patient mix-up may occur.

SUMMARY OF THE INVENTION

In view of the foregoing circumstances, it is an object of the present invention to provide, for example, an apparatus capable of preventing the creation of a chart (information concerning a person under management) having different patient's identification information (identification information of a person under management) and a photograph (photograph of a person under management).

In order to achieve the foregoing objects, according to an aspect of the present invention, an information management system is provided including a first apparatus and a second apparatus. The first apparatus includes an issuing unit for issuing identification information of a specific person. The second apparatus includes an obtaining unit for obtaining the identification information issued by the issuing unit of the first apparatus; an image capturing unit for capturing an image of the specific person; and an output unit for associating, in order to manage management information for the specific person, the identification information obtained by the obtaining unit with an image corresponding to image data obtained as a result of capturing the image by the image capturing unit and for outputting the identification information and the image.

The information management system may further include a third apparatus. The third apparatus may include a reading unit for reading the identification information and the image, which are output from the output unit of the second apparatus and which are associated with each other; and a creation unit for creating a document describing the management information, the document having the identification information and the image read by the reading unit printed thereon.

According to the information management system of the present invention, identification information of a specific person is issued, the issued identification information is obtained, an image of the specific person is captured, and management information for the specific person is managed. To this end, the obtained identification information and an image corresponding to image data obtained as a result of capturing the image are associated with each other and output.

In order to achieve the foregoing objects, according to another aspect of the present invention, an information processing apparatus is provided including an obtaining unit for obtaining issued identification information of a specific person; an image capturing unit for capturing an image of the specific person; and an output unit for associating, in order to manage management information for the specific person, the identification information obtained by the obtaining unit with an image corresponding to image data obtained as a result of capturing the image by the image capturing unit and for outputting the identification information and the image.

In order to achieve the foregoing objects, according to yet another aspect of the present invention, an information processing method is provided including an obtaining step of obtaining issued identification information of a specific person; an image capturing step of capturing an image of the specific person; and an output step of associating, in order to manage management information for the specific person, the identification information obtained in the obtaining step with an image corresponding to image data obtained as a result of capturing the image in the image capturing step and outputting the identification information and the image.

In order to achieve the foregoing objects, according to a further aspect of the present invention, a recording medium having a program recorded therein is provided. The program includes an obtaining control step of controlling obtaining issued identification information of a specific person; an image capturing control step of controlling capturing an image of the specific person; and an output control step of controlling associating, in order to manage management information for the specific person, the identification information obtained in the obtaining control step with an image corresponding to image data obtained as a result of capturing the image in the image capturing control step and outputting the identification information and the image.

In order to achieve the foregoing objects, according to another aspect of the present invention, a program for causing a computer to perform the following steps is provided. The steps include an obtaining control step of controlling obtaining issued identification information of a specific person; an image capturing control step of controlling capturing an image of the specific person; and an output control step of controlling associating, in order to manage management information for the specific person, the identification information obtained in the obtaining control step with an image corresponding to image data obtained as a result of capturing the image in the image capturing control step and outputting the identification information and the image.

According to the information processing apparatus and method and the program, issued identification information of a specific person is obtained, an image of the specific person is captured, and management information for the specific person is managed. To this end, the obtained management information and an image corresponding to image data obtained as a result of capturing the image are associated with each other and output.

BRIEF DESCRIPTION OF THE DRAWINGS

FIG. 5 is a flowchart describing the operation of the photograph booth;

FIG. 15 is a flowchart describing the operation of the photograph booth shown in FIG. 12.

DESCRIPTION OF THE PREFERRED EMBODIMENTS

Figure 1:
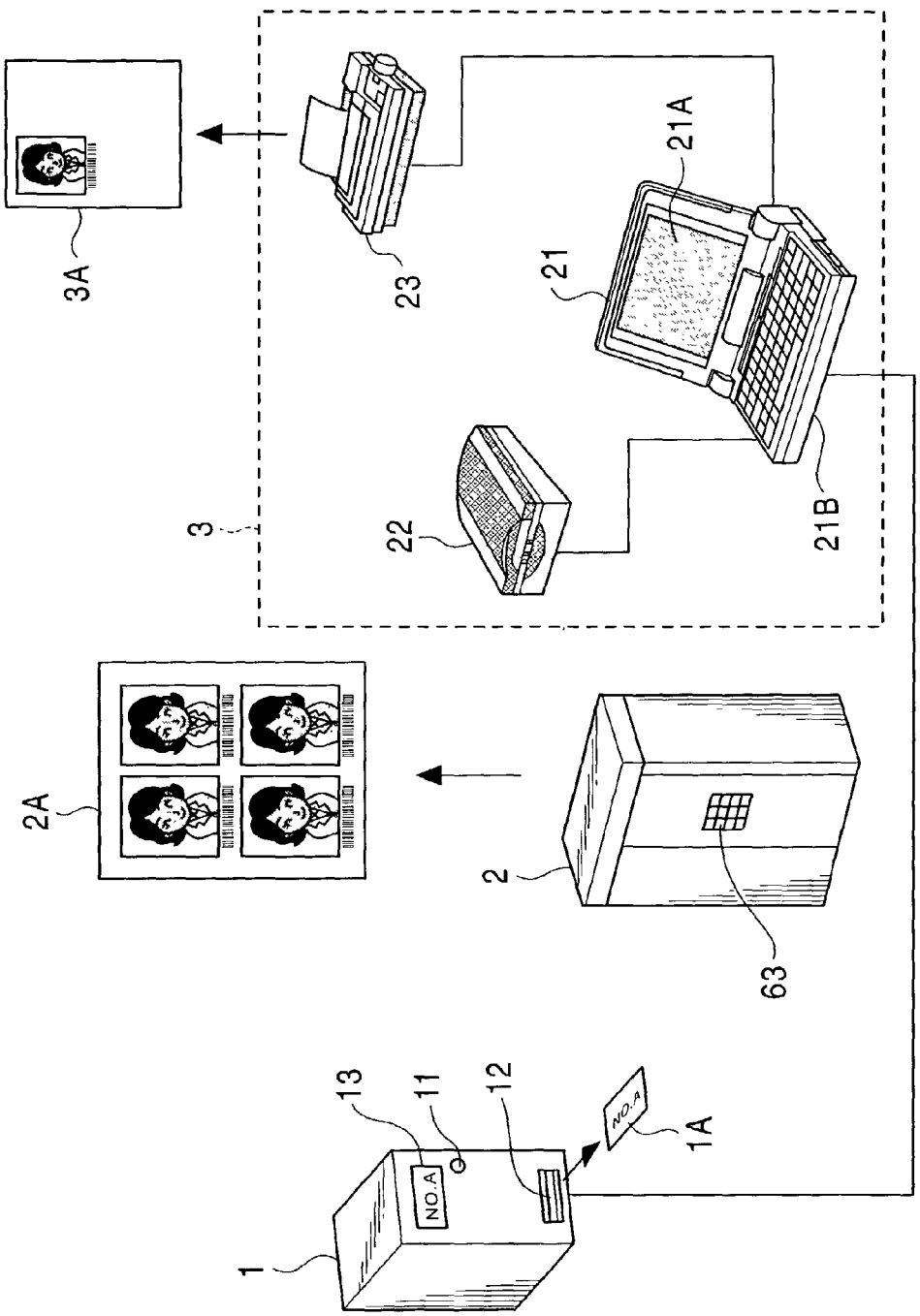
FIG. 1 is an illustration of an example of the configuration of a patient information management system to which the present invention is applied.

FIG. 1 shows an example of the configuration of a system for managing patient information, to which the present invention is applied.

A new patient operates, for example, a button 11 of an identification number issuing apparatus 1 installed in the reception area in a hospital and receives a ticket 1A from a ticket slot 12. The ticket 1A has the patient's identification number printed thereon.

Specifically, the identification number issuing apparatus 1 issues the identification number in response to the operation of the button 11, prints the identification number on the ticket 1A, and ejects the ticket 1A from the ticket slot 12. The identification number issuing apparatus 1 is connected to a management apparatus 3 (personal computer 21). When the identification number is issued, the issued identification number is sent to the management apparatus 3.

The identification number issuing apparatus 1 includes a display unit 13. The display unit 13 can display the issued identification number, and the patient can look at the displayed identification number and can confirm the identification number.

Having received the ticket 1A, the patient moves to a photograph booth 2. The patient operates an identification number input panel 63, inputs the identification number printed on the ticket 1A, and, for example, takes a photograph of the patient's upper body. From the photograph booth 2, for example, a photograph/bar code sheet 2A having printed thereon four pairs including photographs and bar codes, which are disposed so as to vertically correspond to each other, is ejected. The patient receives this photograph/bar code sheet 2A.

More specifically, the photograph booth 2 generates a bar code indicating the identification number input by the patient, prints the bar code so as to correspond to the user's photograph, creates the photograph/bar code sheet 2A, and ejects the photograph/bar code sheet 2A. In this example, the bar code represents the identification number. In addition to the identification number, for example, the bar code can represent the date on which the photograph was taken, a hospital code, or the ID of the photograph booth 2.

Having received the photograph/bar code sheet 2A, the patient moves to, for example, the reception and submits the photograph/bar code sheet 2A and a health insurance card to the attendant at reception.

The attendant operates the personal computer 21 of the management apparatus 3, scans the photograph/bar code sheet 2A using a scanner 22, and prints a chart 3A having printed thereon the scanned photograph and bar code by a printer 23.

When the identification number is sent from the identification number issuing apparatus 1, the personal computer 21 of the management apparatus 3 writes the identification number in a formatted space on the chart 3A and stores the chart 3A on which the identification number is written.

When the attendant performs the operation to create the chart 3A, the personal computer 21 reads the chart 3A on which the identification number indicated by the bar code read from the photograph/bar code sheet 2A using the scanner 22 is written, attaches the photograph which has been read in a similar manner to the chart 3A, and displays the chart 3A on a display unit 21A.

With regard to the chart 3A displayed on the display unit 21A, the attendant operates a keyboard 22A and inputs the patient's name, address, etc., which are obtained from the health insurance card. Then, the personal computer 21 stores the information. When the attendant performs the operation to perform printing, the chart 3A having the bar code, the photograph, and the information recorded thereon is printed by the printer 23.

The printed chart 3A is given to a doctor for the medical examination. The pairs (four pairs) including photographs and bar codes of the photograph/bar code sheet 2A are separated from one another, and each pair is pasted onto a registration card or a nametag.

Since the bar code and the photograph are shown on the chart 3A, the association between the chart 3A and the patient can be easily and accurately confirmed. Thus, patient mix-up is prevented.

Since the photograph/bar code sheet 2A having printed thereon pairs including bar codes and photographs is used, for example, the creation of the chart 3A indicating a different patient's bar code (to be precise, the identification number) and photograph, as a result of pasting a wrong photograph, is prevented.

Since a plurality of pairs including bar codes and photographs is printed (four pairs in the case shown in FIG. 1), each pair can be pasted onto the chart 3A, the registration card, a bed for a hospitalized patient, a nurse center, or a surgical room. Thus, the patient can be confirmed by these pairs including bar codes and photographs.

Figure 2:
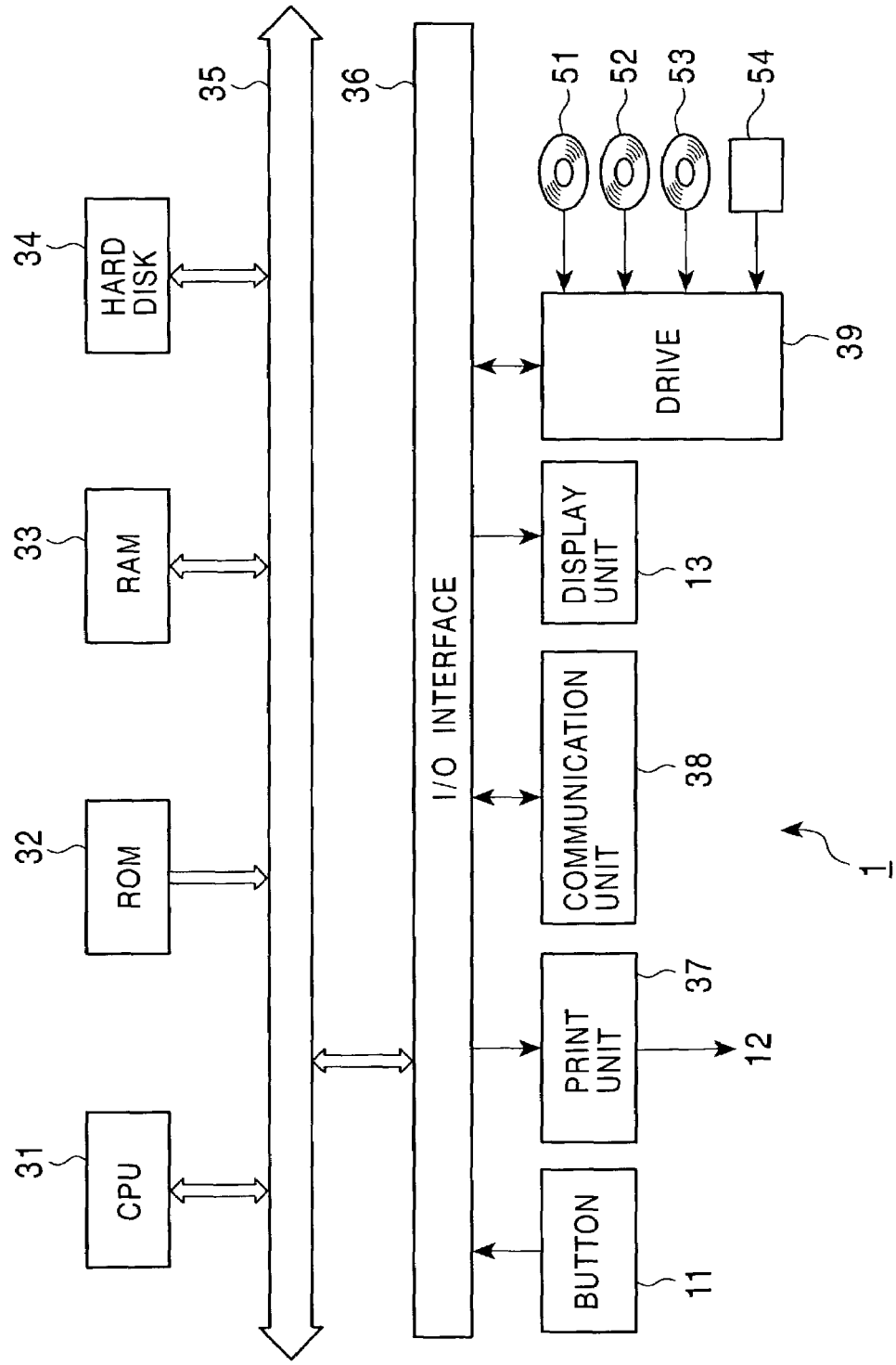
FIG. 2 is a block diagram showing an example of the configuration of an identification number issuing apparatus shown in FIG. 1.

FIG. 2 shows an example of the configuration of the identification number issuing apparatus 1.

An input/output (I/O) interface 36 is connected to a CPU (Central Processing Circuit) 31 via a bus 35. When the CPU 31 receives a command from the button 11 via the I/O interface 36, the CPU 31 loads a program for issuing the identification number, the program being stored in, for example, a ROM (Read Only Memory) 32, a hard disk 34, or a recording medium such as a magnetic disk 51, an optical disk 52, a magneto-optical disk 53, or a semiconductor memory 54 mounted in a drive 39, into a RAM (Random ACCESS MEMORY) 33 and executes the program. The CPU 31 outputs the identification number, which is the processing result, to a print unit 37 via the I/O interface 36 and prints the identification number on the ticket 1A. Also, the CPU 31 outputs the identification number to the display unit 13 formed by an LCD (Liquid Crystal Display) and displays the identification number on the display unit 13. After the identification number is printed on the ticket 1A by the print unit 37, the ticket 1A is issued and ejected from the ticket slot 12.

A communication unit 38 communicates with the management apparatus 3 and transmits the identification number input from the CPU 31 to the management apparatus 3.

Figure 3:
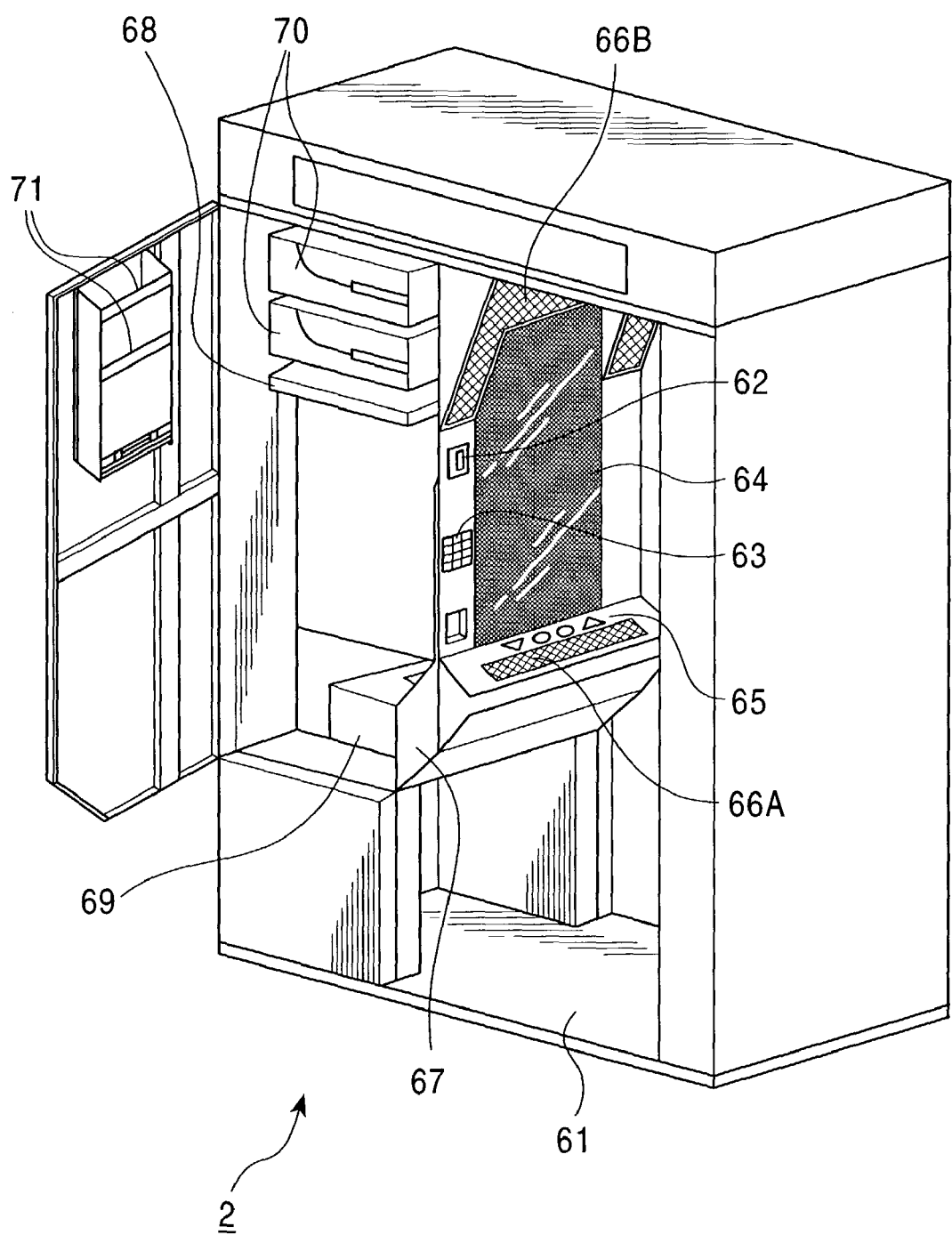
FIG. 3 is an illustration of an example of the external configuration of a photograph booth shown in FIG. 1.

FIG. 3 shows an example of the external configuration of the photograph booth 2.

In a booth 61 of the photograph booth 2, a money slot 62, the identification number input panel 63, by which the identification number printed on the ticket 1A is input, a half mirror 64, an operation panel 65 operated when a photograph is taken, and illuminators 66A and 66B are disposed. The patient sits in a chair (not shown) so as to face the half mirror 64, inserts a predetermined amount of money into the money slot 62, operates the identification number input panel 63 to input the identification number, and operates the operation panel 65 to take a photograph.

On the opposite side of the wall of the interior of the booth 61 where the half mirror 64 is disposed, a money box 67 for containing the money inserted into the money slot 62, a bar code generator 68 for generating a bar code on the basis of the identification number input from the identification number input panel 63, an image capture unit 69 including a camera, and a digital printer (two printers in this example) 70 for printing the bar code generated by the bar code generator 68 and the patient's photograph generated as a result of capturing the image by the image capture unit 69, as shown in FIG. 1, and for ejecting the photograph/bar code sheet 2A from a sheet ejection slot 71 are provided.

Figure 4:
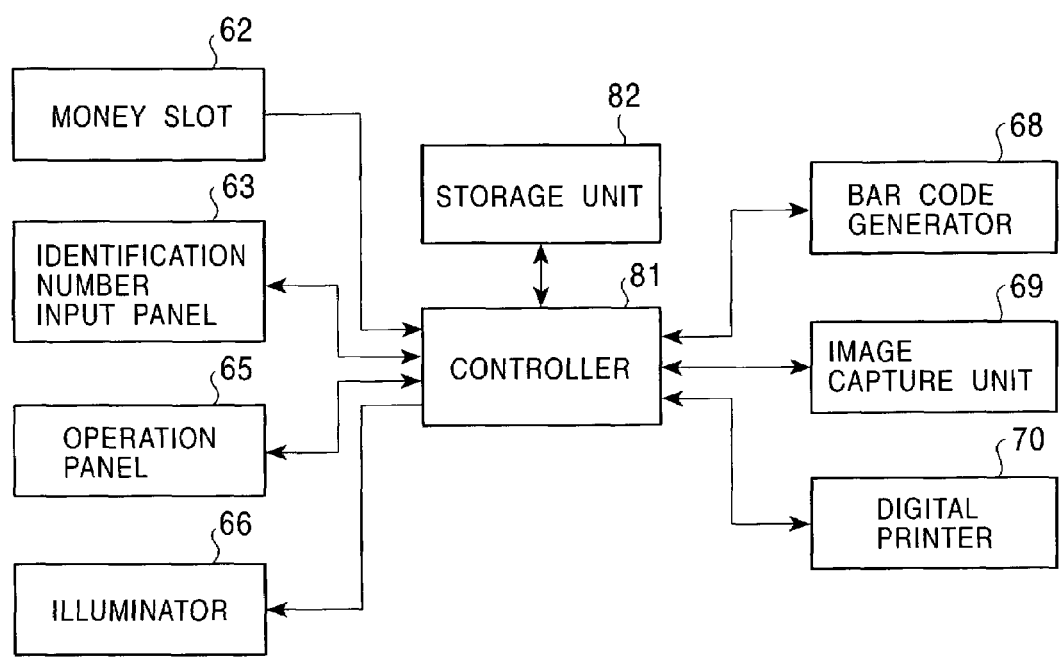
FIG. 4 is a block diagram showing an example of the functional configuration of the photograph booth shown in FIG. 1.

FIG. 4 shows an example of the functional configuration of the photograph booth 2.

A controller 81 obtains, from the identification number input panel 63, the identification number input thereto and stores the identification number in a storage unit 82. Also, the controller 81 appropriately stores image data (photograph data) obtained as a result of capturing the image by the image capture unit 69 in the storage unit 82. The controller 81 controls the components by using the identification number and the photograph data and creates the photograph/bar code sheet 2A. A photograph/bar code sheet creating process will now be described with reference to a flowchart shown in FIG. 5.

In step S1, after the patient inserts a predetermined amount of money into the money slot 62 and operates the identification number input panel 63 to input the identification number printed on the ticket 1A, the controller 81 obtains the identification number from the identification number input panel 63 and controls the bar code generator 68 to generate a bar code representing the identification number. The bar code generator 68 supplies the generated bar code (to be precise, graphic data of the bar code) to the controller 81.

In step S2, when the patient operates the operation panel 65 to input an image capturing start command, the controller 81 controls the image capture unit 69 to perform image-capturing processing. The image capture unit 69 captures an image in front of the half mirror 64 (since the patient is sitting in the chair (not shown) facing the half mirror 64, the image of the patient is captured in this case) and supplies the resultant photograph data to the controller 81. The controller 81 stores the photograph data supplied from the image capture unit 69 in the storage unit 82.

In step S3, the controller 81 controls the digital printer 70 to vertically arrange four bar codes supplied from the bar code generator 68 and four photographs corresponding to the photograph data stored in the storage unit 82 and to print the photograph/bar code sheet 2A. The digital printer 70 prints the photograph/bar code sheet 2A (on the front side or the back side of the chart 3A) and ejects the photograph/bar code sheet 2A from the sheet ejection slot 71.

Subsequently, the process is terminated.

Figure 6B:
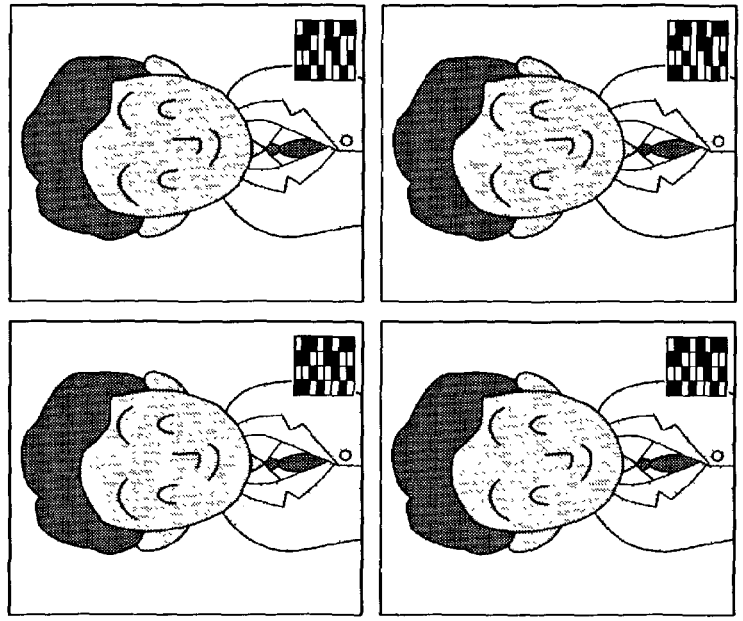
FIGS. 6A and 6B are illustrations of examples of photograph/bar code sheets.
Figure 6A:
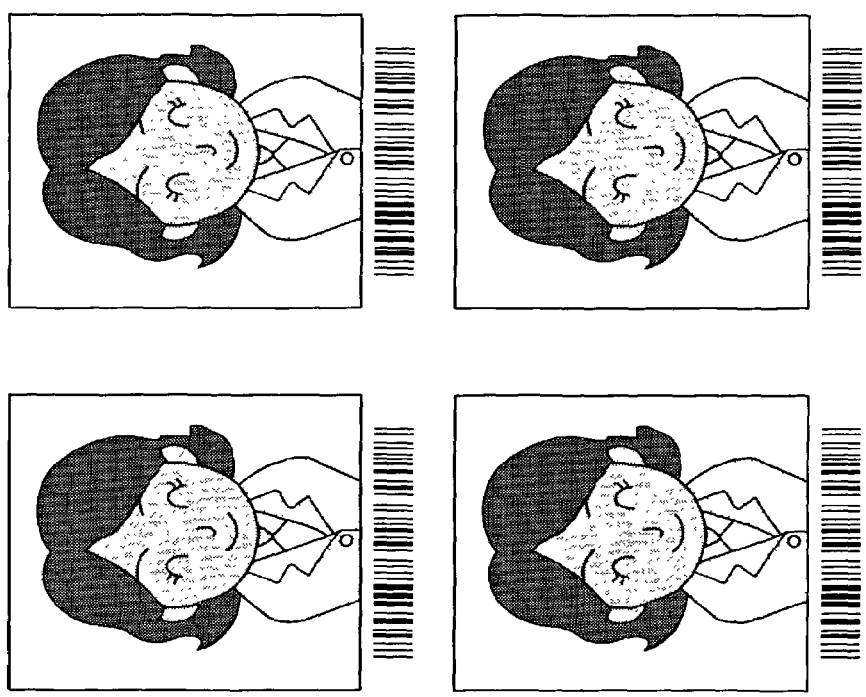

In the foregoing description, a case in which a one-dimensional bar code (FIG. 1 or FIGS. 6A and 6B) has been described. However, as shown in FIG. 6B, two-dimensional bar codes capable of storing information with a higher density can be used. In other words, since the code size can be minimized for two-dimensional bar bodes, two-dimensional bar codes are convenient when a small photograph is used. Possible types of two-dimensional bar codes include PDF-417, Vericode (registered trademark), QR code (Quick Response Code), and MaxiCode.

Figure 7:
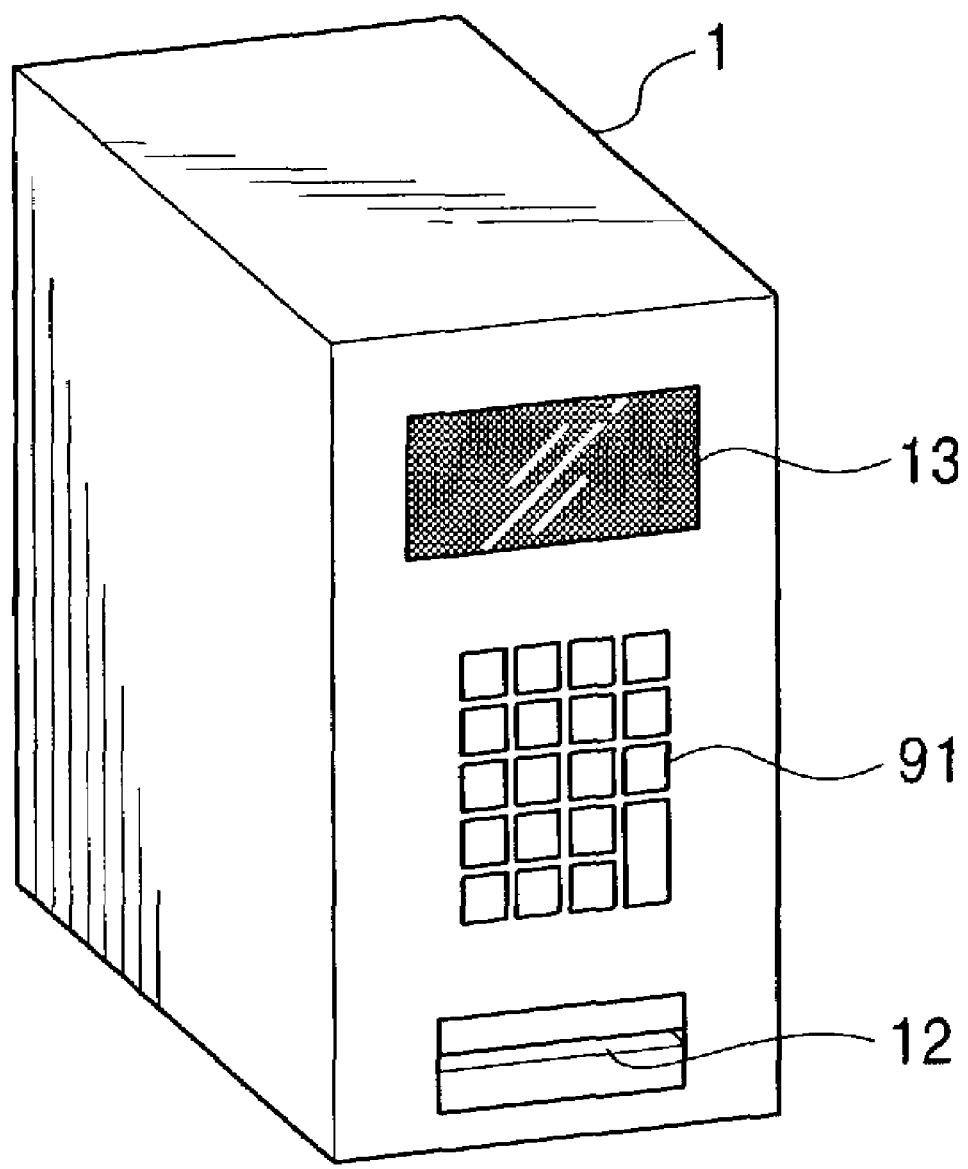
FIG. 7 is an illustration showing another example of the configuration of the identification number issuing apparatus shown in FIG. 1.

In the foregoing description, the identification number issuing apparatus 1 issues an arbitrary identification number. Alternatively, for example, as shown in FIG. 7, an operation unit 91 can be provided, and, for example, the patient is allowed to input the health insurance number of the health care insurance. The identification number issuing apparatus 1 can issue an identification number corresponding to the input health insurance number.

In the foregoing description, the identification number issuing apparatus 1 and the management apparatus 3 are connected to each other. When the identification number issuing apparatus 1 issues an identification number, the identification number is sent to the management apparatus 3. The management apparatus 3 creates and stores, in advance, a chart on which the identification number is written. Alternatively, the identification number issuing apparatus 1 and the management apparatus 3 do not exchange the identification number with each other. The chart 3A is created only when the management apparatus 3 scans the photograph/bar code sheet 2A.

Instead of providing the management apparatus 3, for example, the attendant can cut a pair including a photograph and a bar code from the photograph/bar code sheet 2A and paste the cut photograph and bar code onto the chart 3A. When the photograph and the bar code are pasted by hand, because the photograph is associated with the bar code, the photograph will never be pasted onto the chart 3A having a different patient's identification number.

In the foregoing description, the photographs and the bar codes are vertically disposed on the photograph/bar code sheet 2A. Alternatively, the photographs and the bar codes can be disposed at different positions as long as the photographs are not covered by the bar codes.

In the foregoing description, a case in which the photographs are digitally printed is described. Alternatively, a photograph can be developed and created, and digitalized bar code data can be digitally printed on the photograph.

Figure 8:
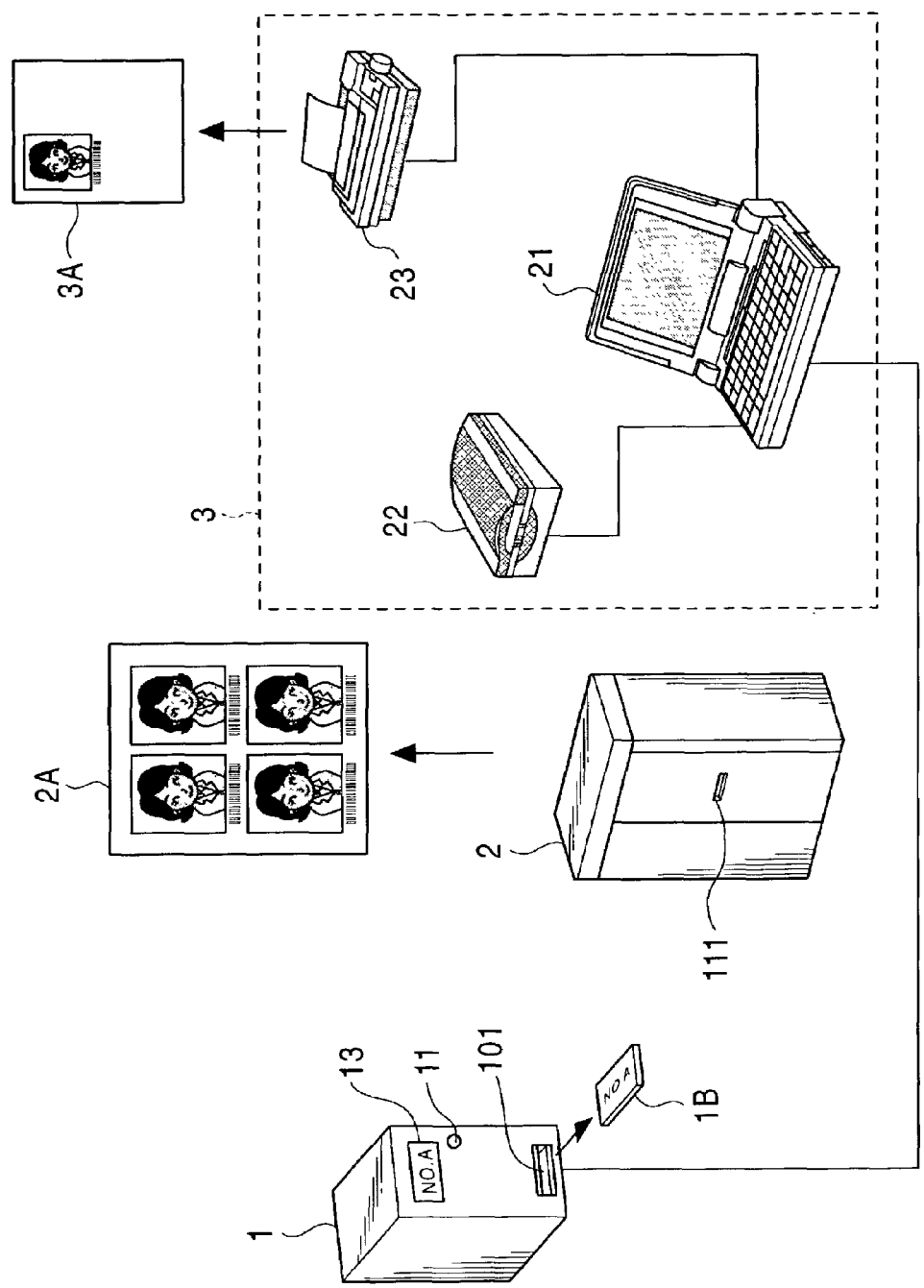
FIG. 8 is an illustration showing another example of the configuration of a patient information management system to which the present invention is applied.

FIG. 8 shows another example of the configuration of a patient information management system to which the present invention is applied. In this example, the identification number issuing apparatus 1 has a card ejection slot 101 in place of the ticket slot 12 shown in FIG. 1. Instead of ejecting the ticket 1A, the identification number issuing apparatus 1 ejects a memory card 1B having the identification number stored therein from the card ejection slot 101.

Figure 9:
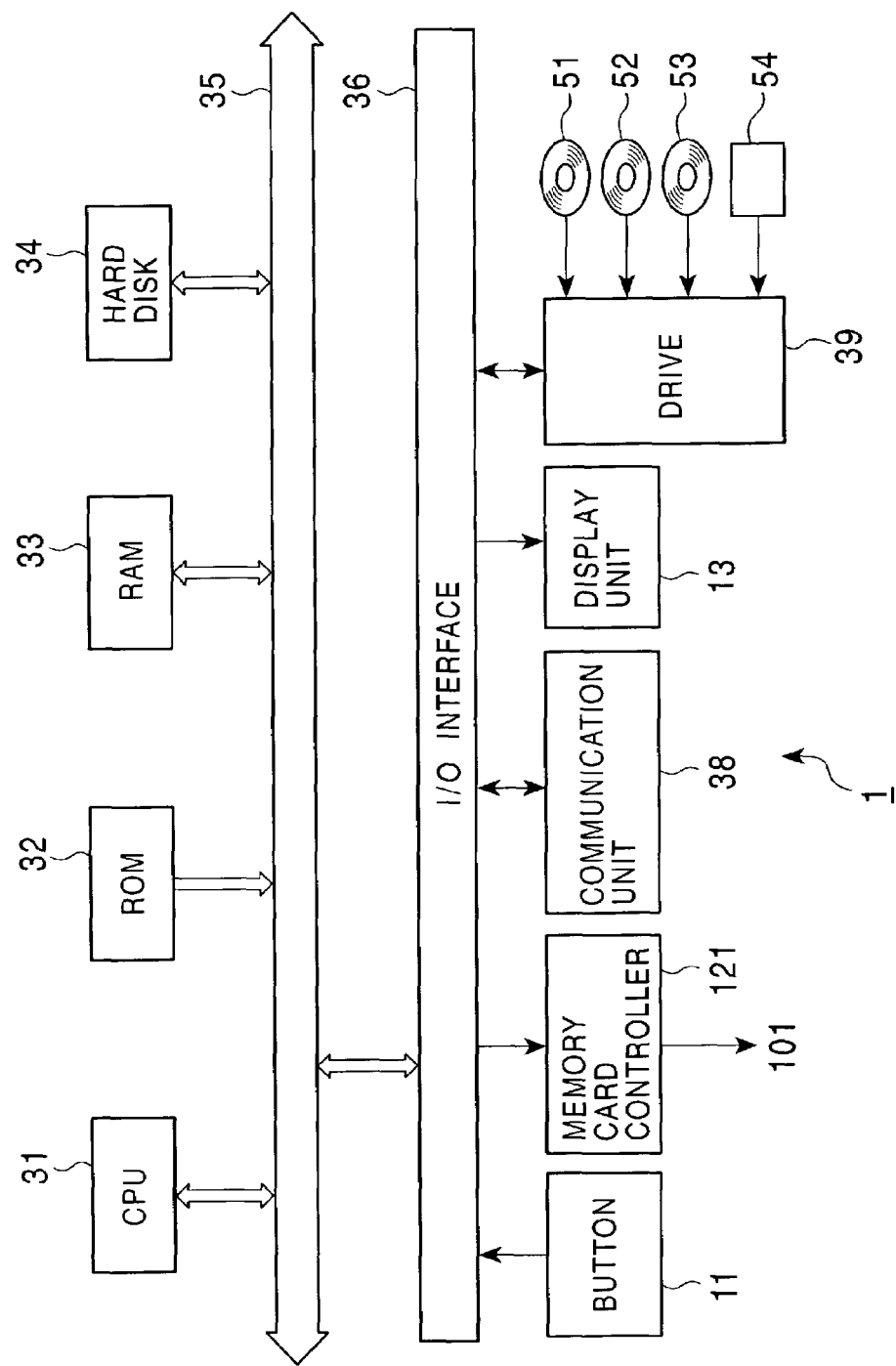
FIG. 9 is a block diagram showing an example of the configuration of an identification number issuing apparatus shown in FIG. 8.

FIG. 9 shows an example of the configuration of the identification number issuing apparatus 1 shown in FIG. 8. In this identification number issuing apparatus 1, a memory card controller 121 is provided in place of the print unit 37 shown in FIG. 2. The memory card controller 121 writes the identification number input from the CPU 31 to the memory card 1B, and the memory card 1B is ejected from the card ejection slot 101.

Figure 10:
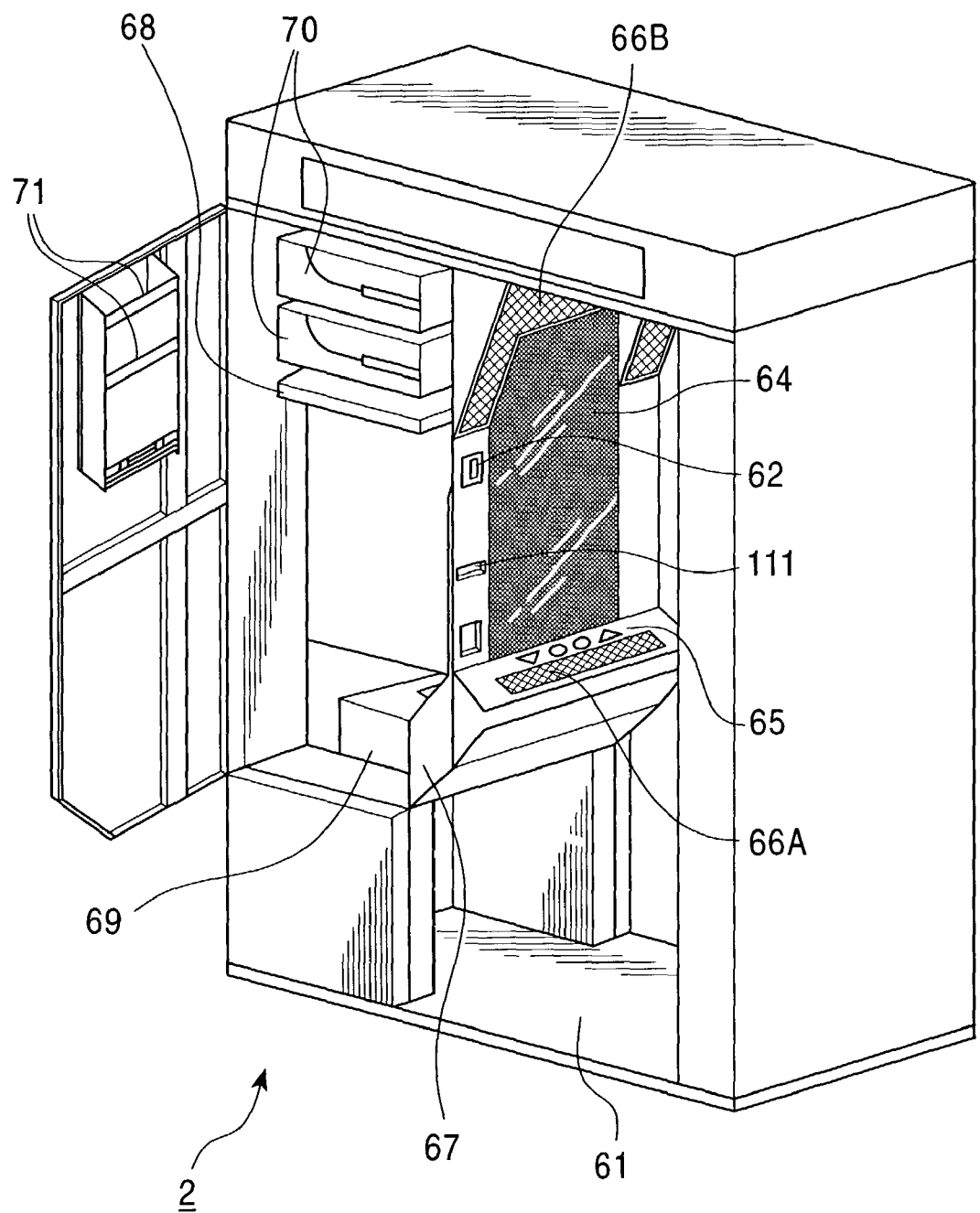
FIG. 10 is an illustration showing an example of the external configuration of a photograph booth shown in FIG. 8.

In the photograph booth 2, as shown in FIG. 10, a memory card insertion slot 111 into which the memory card 1B is inserted is provided in place of the identification number input panel 63 shown in FIGS. 1 and 3. Specifically, in this example, the photograph booth 2 reads an identification number from the memory card 1B inserted in the memory card insertion slot 111 and generates a bar code representing the read identification number.

The photograph booth 2 can store photograph data obtained as a result of capturing an image of the patient in the memory card 1B. Specifically, in this example, the management apparatus 3 can scan the photograph data and the bar code from the photograph/bar code sheet 2A using the scanner 22 or can read the photograph data and the bar code from the memory card 1B inserted into an insertion slot (not shown) of the personal computer 21.

Figure 11:
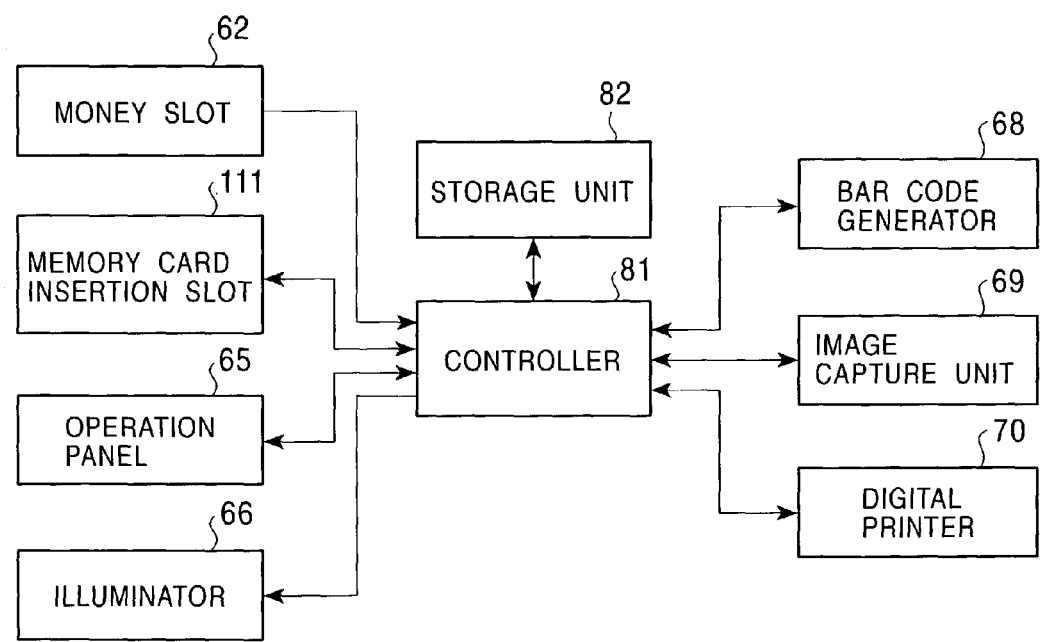
FIG. 11 is a block diagram showing an example of the functional configuration of the photograph booth shown in FIG. 8.

FIG. 11 shows an example of the functional configuration of the photograph booth 2 shown in FIG. 8. The controller 81 reads the identification number from the memory card 1B inserted in the memory card insertion slot 111 and stores photograph data captured by the image capture unit 69 in the storage unit 82. The controller 81 controls the components on the basis of the read identification number and the photograph data stored in the storage unit 82 and creates the photograph/bar code sheet 2A.

The controller 81 stores the photograph data stored in the storage unit 82 in the memory card 1B inserted in the memory card insertion slot 111.

Figure 12:
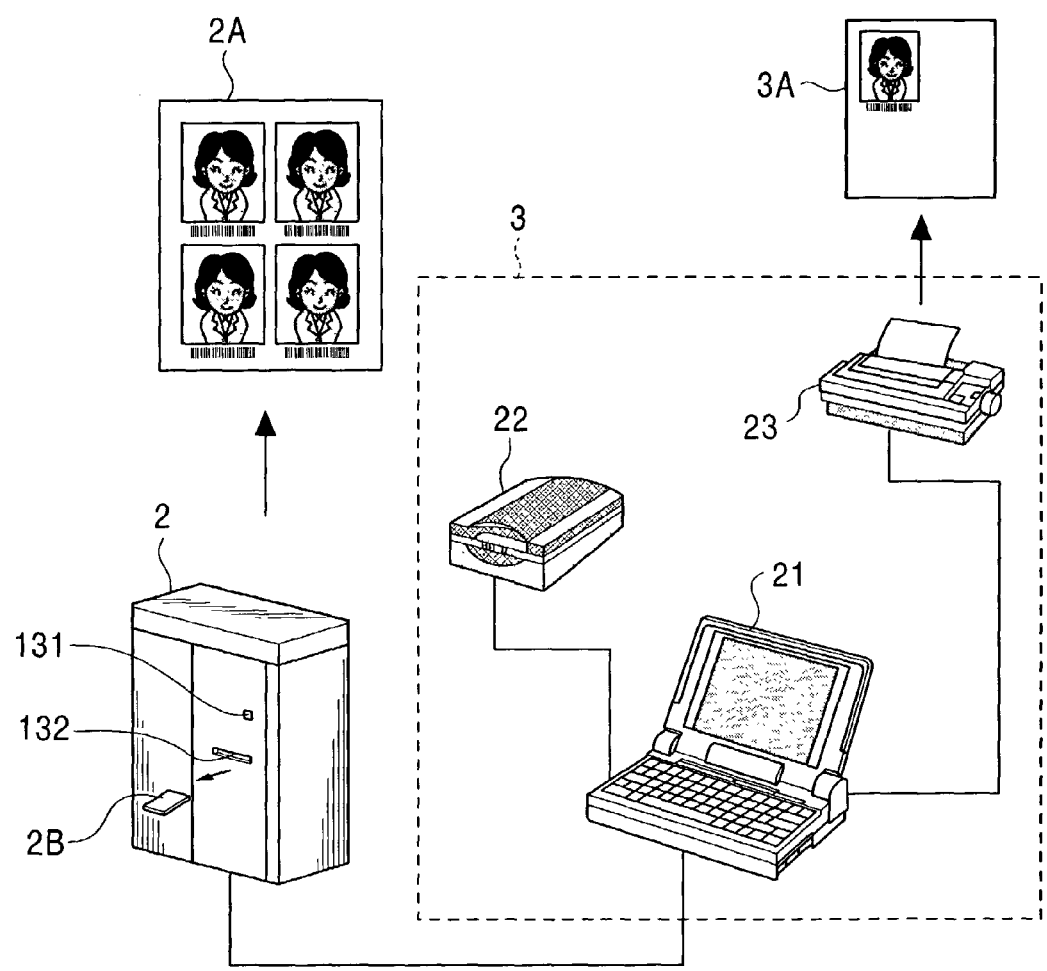
FIG. 12 is an illustration showing another example of the configuration of a patient information management system to which the present invention is applied.

FIG. 12 shows another example of a patient information management system to which the present invention is applied.

In this example, the identification number issuing apparatus 1 shown in FIG. 8 is provided in the photograph booth 2. In other words, the photograph booth 2 is provided with, as shown in FIGS. 12 and 13, a button 131 corresponding to the button 11 of the identification number issuing apparatus 1 and a card ejection slot 132 corresponding to the card ejection slot 101 of the identification number issuing apparatus 1.

Figure 13:
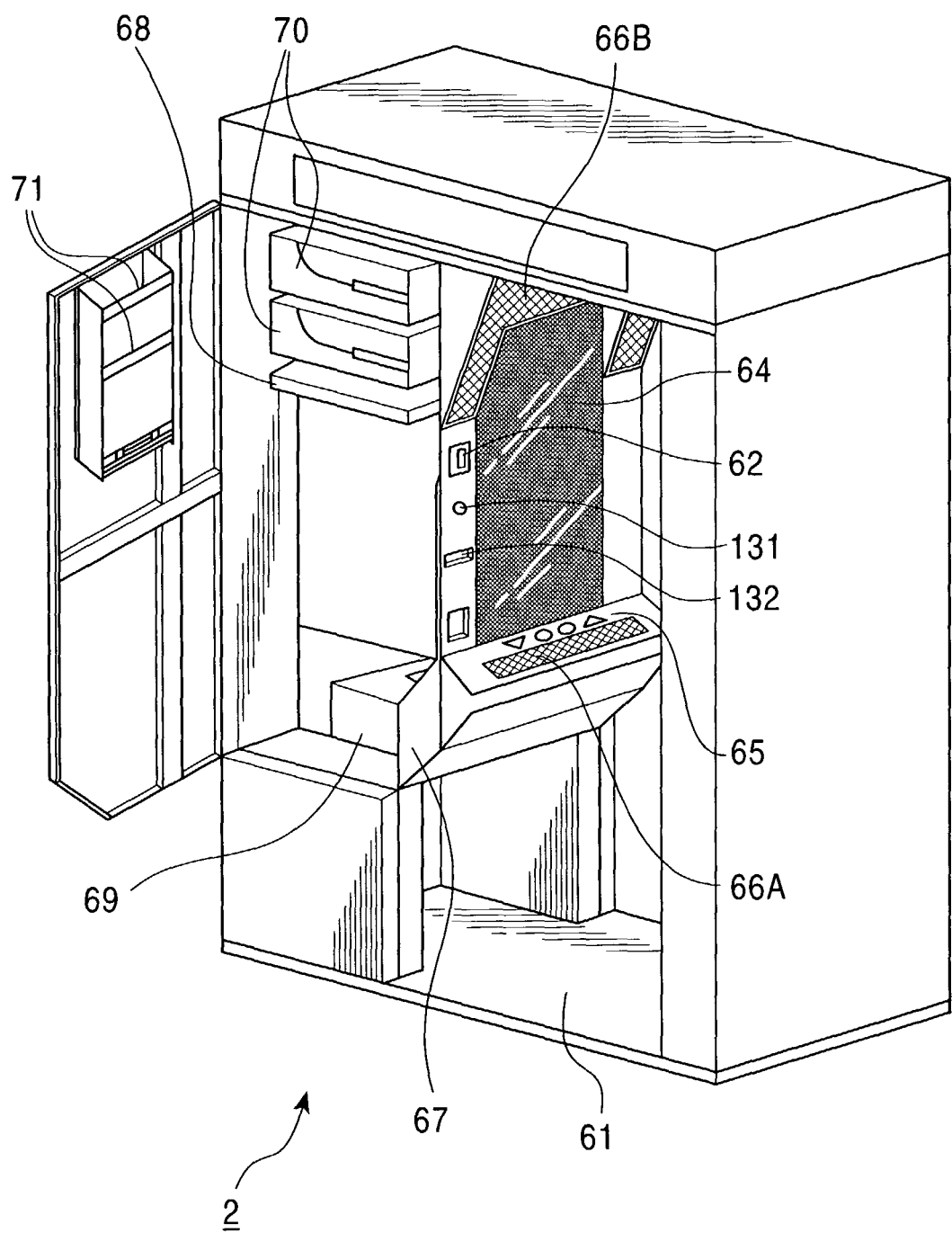
FIG. 13 is an illustration showing an example the external configuration of a photograph booth shown in FIG. 12.

As shown in FIG. 13, the photograph booth 2 issues an identification number in accordance with the operation of the button 131 and stores the identification number in a memory card 2B (not shown). The photograph booth 2 generates a bar code representing the issued identification number, prints the bar code corresponding to the captured photograph of the patient, creates the photograph/bar code sheet 2A, and outputs the photograph/bar code sheet 2A.

The photograph booth 2 stores the patient's photograph data in the memory card 2B and ejects the memory card 2B from the card ejection slot 132.

Figure 14:
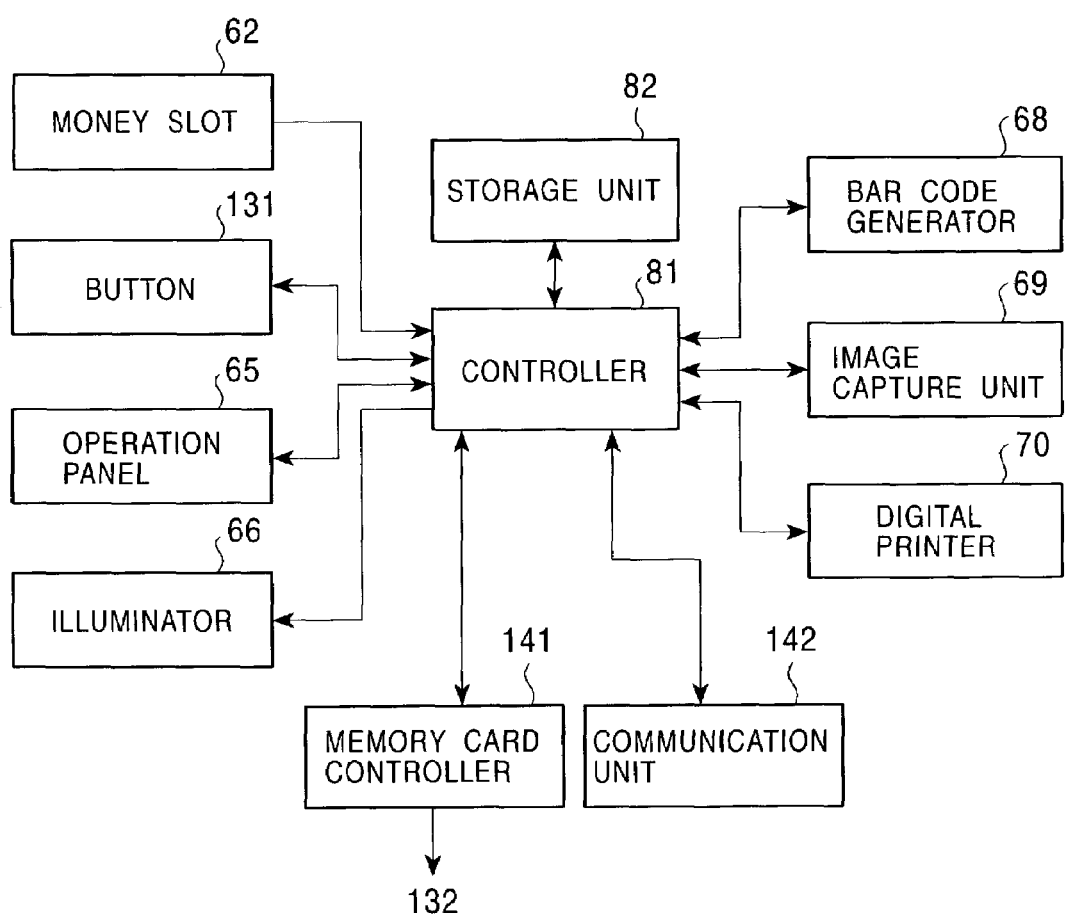
FIG. 14 is a block diagram showing an example of the functional configuration of the photograph booth shown in FIG. 12.

FIG. 14 shows an example of the functional configuration of the photograph booth 2 shown in FIG. 12. In this case, the controller 81 issues by itself an identification number and appropriately stores photograph data obtained as a result of capturing an image by the image capture unit 69 in the storage unit 82. The controller 81 controls the components on the basis of the issued identification number and the photograph data stored in the storage unit 82 and creates the photograph/bar code sheet 2A.

Also, the controller 81 controls a memory card controller 141 to store the identification number and the photograph data in the memory card 2B.

When the controller 81 issues the identification number, the controller 81 transmits the identification number to the management apparatus 3 through a communication unit 142.

The flowchart shown in FIG. 15 represents processing steps of a photograph/bar code sheet creating process performed by the photograph booth 2 shown in FIG. 12.

In step S11, after a patient inserts a predetermined amount of money into the money insertion slot 62 and operates the button 131, the controller 81 issues an identification number.

In step S12, the controller 81 controls the bar code generator 68 and generates a bar code representing the identification number issued in step S11. The bar code generator 68 supplies the generated bar code (to be precise, graphic data of the bar code) to the controller 81. At this time, the controller 81 controls the communication unit 142 and sends the issued identification number to the management apparatus 3. Accordingly, the management apparatus 3 (personal computer 21) writes the identification number sent from the photograph booth 2 into a formatted space on the chart and stores the chart 3A.

In step S13, when the controller 81 receives a capturing start command in response to the operation of the operation panel 65 by the patient, the controller 81 controls the image capture unit 69 to capture an image, and the captured image data (photograph data) is stored in the storage unit 82.

In step S14, the controller 81 controls the digital printer 70 to print the photograph/bar code sheet 2A generated by vertically disposing, as shown in FIG. 12, four bar codes supplied in step S12 from the bar code generator 68 and four pieces of photograph data supplied in step S13 from the image capture unit 69.

In step S15, the controller 81 controls the memory card controller 141 to store the identification number issued in step S11 and the photograph data obtained in step S13 in the memory card 2B and ejects the memory card 2B from the card ejection slot 132.

Subsequently, the process is terminated.

In the foregoing description, a case in which patients are under management is described. Alternatively, for example, members (members of a sports club or students at an English school) can be managed by pasting photographs and bar codes onto membership cards.

The above series of processes can be performed by a general personal-purpose computer.

The personal computer includes a packaged media having a program for executing the foregoing processes stored therein, the packaged media being distributed to offer the program to users, such as a magnetic disk (including a floppy disk), an optical disc (including a CD-ROM (Compact Disc-Read Only Memory) and a DVD (Digital Versatile Disc)), and a magneto-optical disc (including an MD (Mini Disc)), and a semiconductor memory. Also the personal computer includes a ROM or a hard disk incorporated therein beforehand to be distributed to users.

In the present description, steps for writing a program not only include time-series processing performed in accordance with the described order but also include parallel or individual processing, which may not necessarily be performed in time series.

As described above, according to an information management system of the present invention, identification information of a specific person is issued, the issued identification is obtained, an image of the specific person is captured, and management information for the specific person is managed. To this end, the obtained identification information and an image corresponding to image data obtained as a result of capturing the image are associated with each other and output. Thus, the management information can be appropriately managed.

Furthermore, according to an information processing apparatus and method and a program of the present invention, issued identification information of a specific person is obtained, an image of the specific person is captured, and management information for the specific person is managed. To this end, the obtained identification information and an image corresponding to image data obtained as a result of capturing the image are associated with each other and output. Thus, the management information can be appropriately managed.

What is claimed is:

1. An information management system for an individual comprising:
   means for capturing an image of the individual;
   output means for providing, immediately after capturing the image, a second item having at least the identification information and the captured image thereon;
   reading means for reading the identification information and the captured item on the second item; and
   creation means for creating a third item describing management information, the third item having the identification information and the captured image printed thereon.

2. An information management system according to claim 1, further comprising:
   storage means for storing the identification information in a portable storage unit; and
   means for obtaining the identification information from the portable storage unit, wherein
   the image capturing means stores the captured image in the portable storage unit, and wherein
   the reading means reads the identification information from the portable storage unit.

3. An information management system according to claim 1, wherein the output means prints, on the second item, at least one pair including a code representing the identification information and the captured image, the code and the captured image being disposed so as to be associated with each other.

4. An information management system according to claim 3, wherein the code is a one-dimensional bar code or a two-dimensional bar code.

5. An information management system according to claim 1, wherein the output means outputs, on the second item, a pair including a code representing the identification information and the captured image, the code and the captured image being disposed so as to be associated with each other.

6. An information management system according to claim 1, further comprising:
   means for presenting the first item having the identification information provided thereon to the individual;
   input means for inputting the first item having the identification information provided thereon; and
   means for obtaining the identification information provided on the first item.

7. An information management system according to claim 6, wherein the first item is a ticket on which the identification information is written or a display on which the identification information is displayed.

8. An information management system according to claim 1, further comprising:
   storage means for storing the identification information in a portable storage unit; and
   means for obtaining the identification information from the portable storage unit.

9. An information management system according to claim 1, further comprising:
   means for inputting personal information on the individual, wherein the issuing means issues the first item having the identification information provided thereon in association with the inputted personal information.

10. An information management system according to claim 1, wherein the first item is a ticket.

11. An information management system according to claim 1, wherein the first item is a memory card.

12. An information management system according to claim 1, wherein the first item is a display.

13. An information management system according to claim 1, wherein the second item is a photograph/bar code sheet.

14. An information management system according to claim 1, wherein the identification information includes an identification number.

15. An information management system according to claim 1, wherein the third item is a document.

16. An information processing apparatus comprising:
    means for issuing a first item having identification information for an individual provided thereon;
    means for capturing an image of the individual;
    output means for associating on a second item, immediately after obtaining the captured image, the identification information with the captured image and for outputting the second item;
    reading means for reading the identification information and the captured item on the second item; and creation means for creating a third item describing management information, the third item having the identification information and the captured image printed thereon.

17. An information processing apparatus according to claim 16, wherein the output means prints, on the second item, at least one pair including a code representing the identification information and the captured image, the code and the captured image being disposed so as to be associated with each other.

18. An information processing apparatus according to claim 17, wherein the code is a one-dimensional bar code or a two-dimensional bar code.

19. An information processing apparatus according to claim 16, wherein the output means outputs, on the second item, a pair including a code representing the identification information and the captured image, the code and the captured image being disposed so as to be associated with each other, and wherein the output means stores the pair in a recording medium.

20. An information processing method comprising:
   a step of issuing a first item having identification information for an individual provided thereon;
   an image capturing step of capturing an image of the individual;
   an output step of associating on a second item, immediately after obtaining the captured image, the identification information with the captured image and outputting the second item;
   a reading step of reading the identification information and the captured item on the second item; and
   a creation step of creating a third item describing management information, the third item having the identification information and the captured image printed thereon.

21. A recording medium having a computer-readable program recorded therein, the program comprising:
   a step of issuing a first item having identification information for an individual provided thereon;
   an image capturing step of capturing an image for the individual; and
   an output step of associating on a second item, immediately after obtaining the captured image, the identification information with the captured image and outputting the second item;
   a reading step of reading the identification information and the captured item on the second item; and
   a creation step of creating a third item describing management information, the third item having the identification information and the captured image printed thereon.

22. A program for causing a computer to perform the following steps, comprising:
   an obtaining step of obtaining issued identification information for an individual from a first item;
   an image capturing step of capturing an image of the individual; and
   an output step of associating on a second item, immediately after obtaining the captured image, the identification information with the captured image and outputting the second item;
   a reading step of reading the identification information and the captured item on the second item; and
   a creation step of creating a third item describing management information, the third item having the identification information and the captured image printed thereon.

* * * * *